United States Patent
Coumanne

(10) Patent No.: US 12,290,593 B2
(45) Date of Patent: May 6, 2025

(54) BUTTER PREPARATION PROCESS

(71) Applicant: NATUROCHIM, Gif-sur-Yvette (FR)

(72) Inventor: Claudine Coumanne, Gif-sur-Yvette (FR)

(73) Assignee: NATUROCHIM, Gif-sur-Yvette (FR)

( * ) Notice: Subject to any disclaimer, the term of this patent is extended or adjusted under 35 U.S.C. 154(b) by 0 days.

(21) Appl. No.: 17/406,500

(22) Filed: Aug. 19, 2021

(65) Prior Publication Data

US 2022/0096359 A1    Mar. 31, 2022

(30) Foreign Application Priority Data

Aug. 19, 2020 (FR) ....................... 2008567

(51) Int. Cl.
| | | |
|---|---|---|
| *A61K 8/9789* | (2017.01) | |
| *A61K 8/67* | (2006.01) | |
| *A61K 8/92* | (2006.01) | |
| *A61Q 5/00* | (2006.01) | |
| *A61Q 5/12* | (2006.01) | |
| *C11C 3/12* | (2006.01) | |

(52) U.S. Cl.
CPC .............. *A61K 8/922* (2013.01); *A61K 8/678* (2013.01); *A61K 8/9789* (2017.08); *A61Q 5/002* (2013.01); *A61Q 5/12* (2013.01); *C11C 3/12* (2013.01)

(58) Field of Classification Search
CPC ........................................................ A61K 8/922
See application file for complete search history.

(56) References Cited

U.S. PATENT DOCUMENTS 8,709,453 B2 *   4/2014   Cap ........................ A61Q 17/04
                                                              424/59

FOREIGN PATENT DOCUMENTS

| CN | 109044889 A | 12/2018 |
| CN | 109431922 A | 3/2019 |
| DE | 202006005804 U1 | 7/2006 |
| KR | 101838642 B1 * | 3/2018 |

OTHER PUBLICATIONS

Cosmetics and Toiletries (https://www.cosmeticsandtoiletries.com/cosmetic-ingredients/moisturizing/article/21834773/comparatively-speaking-natural-vs-hydrogenated-butters) Aug. 2, 2011 (Year: 2011).*
Song (Analysis of Trans Fat in Edible Oils with Cooking Process, Toxicol.Res. vol. 3, pp. 307-312 (2015)) (Year: 2015).*
KR101838642B1 translated doc Mar. 14, 2018 (Year: 2018).*
PCT/FR2008567, Search Report and Written Opinion Dated May 7, 2021, 7 pages.

* cited by examiner

*Primary Examiner* — J. E. Angell
*Assistant Examiner* — Jacob A Boeckelman
(74) *Attorney, Agent, or Firm* — Michael Byrne; Wolter VanDyke Davis PLLC

(57) ABSTRACT

The present invention relates to a butter comprising a vegetable oil and said hydrogenated vegetable oil.

11 Claims, No Drawings

BUTTER PREPARATION PROCESS

FIELD OF THE INVENTION

The present invention relates to butters intended to be used in cosmetic compositions, to the process for the preparation of these butters and also to the cosmetic compositions comprising these butters.

TECHNICAL BACKGROUND

Today, consumer demand as regards cosmetic products is increasingly turning towards natural products and products of biological origin. Consumers are thus more careful with regard to the components of their hygiene and cosmetic products, which results in an increase in the sales of biological cosmetic products of more than 5% per year.

The ingredients experiencing true success include vegetable oils. Vegetable oils are extracted from seeds or fruits and exhibit nourishing and protective properties for the skin and hair.

Furthermore, vegetable oils can be converted into butters, which exhibit similar properties to the vegetable oils. The difference with respect to the oils lies in the fact that they are solid at ambient temperature and become liquid again when they are heated; they thus have the advantage of contributing both the benefits of oils and a texture which makes it possible to obtain finished products having different formulation forms.

Generally, the butters are prepared by hydrogenation of an inexpensive oil, such as sunflower oil, and the addition of another vegetable oil to this hydrogenated oil in order to obtain the texture of a butter. By way of example, the term "apricot butter" will be used if the vegetable oil added to the hydrogenated oil is apricot oil.

Hydrogenation is the process by which hydrogen is added to the points of unsaturation of a fatty acid. The oil is reacted with hydrogen at high temperature and high pressure in the presence of a catalyst. The hydrogenation may or may not be complete, resulting in a hydrogenated oil, of solid consistency, or a partially hydrogenated oil, of semisolid consistency.

However, hydrogenation at high temperature and pressure results in the degradation of temperature-sensitive vegetable oils and the formation of byproducts due to cracking or to condensation which are not desired in cosmetic products. In addition, the method of preparation of the butters which is described above has the disadvantage that the profile of the fatty acids of the butter is less typical of that of the vegetable oil added.

Thus, there exists a need to provide a process for obtaining butter from a single vegetable oil in order to obtain a fatty acid profile typical of the vegetable oil used and which is more friendly to this oil.

SUMMARY OF THE INVENTION

The present invention emerges from the finding by the inventors that a butter prepared from a single vegetable oil exhibits advantageous properties, in particular a profile of fatty acids which is typical of said vegetable oil, for use in cosmetic compositions.

Thus, the present invention relates to a butter comprising a vegetable oil and said hydrogenated vegetable oil.

The present invention also relates to a butter constituted of a vegetable oil, of said hydrogenated vegetable oil and of vitamin E.

The present invention also relates to a process for the preparation of butter intended to be used in cosmetic compositions, from a vegetable oil, comprising the following steps:
 a step of hydrogenation of the vegetable oil;
 a step of addition of the vegetable oil to the hydrogenated vegetable oil, so as to obtain a butter;
 optionally a stage of deodorization.

The present invention also relates to a butter intended to be used in cosmetic compositions which is capable of being prepared or prepared according to the process defined above.

The present invention also relates to a cosmetic composition comprising at least one butter as defined above or prepared by the process as defined above.

DETAILED DESCRIPTION OF THE INVENTION

Butter

Preferably, the butter according to the invention is a butter of vegetable origin. The expression "butter of vegetable origin" according to the invention denotes a butter obtained from a vegetable source, in particular an oil, and which has a solid consistency at ambient temperature, i.e. at a temperature of between 15 and 25° C., at a pressure of 1 atmosphere.

Preferably, the butter according to the invention is of natural origin. As intended herein, the expression "butter of natural origin" according to the invention means a butter consisting solely of ingredients of natural origin.

Preferably, the butter according to the invention is biological. As intended herein, the expression "biological butter" according to the invention means a butter obtained from at least to 95% of material resulting from biological agriculture.

As understood here, the butter according to the invention is not an emulsion. The term "emulsion" is understood to mean a heterogeneous mixture of two immiscible liquids substances. Thus, the butter according to the invention comprises essentially no water or hydrophilic phase.

Preferably, the butter according to the invention is constituted of a vegetable oil, of said hydrogenated vegetable oil and optionally of vitamin E.

Preferably also, the butter according to the invention does not comprise addition of at least one unsaponifiable. The term "unsaponifiable" of a vegetable oil is understood to mean the residual water-insoluble fraction after saponification of the vegetable oil.

By way of example of butter according to the invention it is possible to cite almond butter, apricot butter, argan butter, avocado butter, coconut butter, olive butter, macadamia butter, jojoba butter, hazelnut butter, sea buckthorn butter, fig butter, raspberry butter, sesame butter, oat butter, cherry plum butter, plum butter, pistachio butter, hemp butter and desert date butter.

Preferably, the butter according to the invention is selected from the group consisting of almond butter, apricot butter, argan butter, avocado butter, coconut butter, plum butter, pistachio butter, oat butter and olive butter.

Preferably, the butter according to the invention comprises a vegetable oil and the hydrogenated vegetable oil. As will be clearly apparent to a person skilled in the art, according to the invention, the vegetable oil and the hydrogenated vegetable oil are identical except as regards the hydrogenation; in particular, the hydrogenated vegetable oil according to the invention derives from the vegetable oil by hydrogenation of the latter. Advantageously, the vegetable oil and said hydrogenated vegetable oil according to the invention mix more intimately than two oils originating from different sources; this results in a more stable butter, which has less tendency to phase-separate than the butters obtained from a mixture of oils. Advantageously also, the use of a single vegetable oil for the manufacture of butter makes it possible to obtain a butter having characteristics similar to those of the vegetable oil used. In particular, the butters obtained from one and the same oil exhibit a profile of fatty acids which is typical of the oil used.

The term "vegetable oil" is understood to mean any vegetable oil known to a person skilled in the art capable of being used in a cosmetic composition.

Preferably, the vegetable oil according to the invention is extracted from seeds or from fruits, in particular by pressing or by extraction with supercritical $CO_2$.

Preferably, the vegetable oil according to the invention is natural. The term "natural oil" is understood to mean an oil originating from a plant, in particular from a fruit or from its seeds.

Preferably, the vegetable oil according to the invention is biological. The term "biological oil" is understood to mean an oil resulting, at least to 95%, from biological agriculture.

By way of example of vegetable oil according to the invention it is possible to cite plum oil, pistachio oil, almond oil, apricot oil, argan oil, avocado oil, coconut oil, olive oil, macadamia oil, jojoba oil, hazelnut oil, sea buckthorn oil, fig oil, raspberry oil, sesame oil, oat oil, cherry plum oil, hemp oil and desert date oil.

Preferably, the vegetable oil according to the invention is selected from the group consisting of plum oil, pistachio oil, almond oil, apricot oil, argan oil, avocado oil, coconut oil, oat oil and olive oil.

Preferably, the butter according to the invention comprises between 20% and 98%, more preferably between 30% and 90%, by weight of hydrogenated vegetable oil, with respect to the total weight of the butter.

Preferably, the butter according to the invention comprises between 2% and 80%, more preferably between 10% and 70%, by weight of vegetable oil, with respect to the total weight of butter.

Preferably, the plum butter, pistachio butter, almond butter, apricot butter, argan butter, avocado butter, oat butter and olive butter according to the invention comprise between 45% and 80%, preferably between 50% and 72%, by weight of vegetable oil and between 20% and 55%, preferably between 30% and 50%, by weight of the hydrogenated vegetable oil, with respect to the total weight of butter.

Preferably, the coconut butter according to the invention comprises between 2% and 20%, preferably between 5% and 15%, by weight of vegetable oil and between 80% and 98%, preferably between 85% and 95%, by weight of the hydrogenated vegetable oil, with respect to the total weight of butter.

Preferably, the butter according to the invention additionally comprises vitamin E. Preferably, the butter according to the invention comprises between 0.1% and 0.5%, more preferably between 0.2% and 0.3%, by weight of vitamin E, with respect to the total weight of butter.

Preferably, the plum butter according to the invention comprises between 32% and 54%, more preferably between 37% and 48%, by weight of hydrogenated plum oil and between 46% and 68%, more preferably between 52% and 63%, by weight of plum oil, with respect to the total weight of plum butter. Preferably, the plum butter according to the invention comprises approximately 0.2% by weight of vitamin E, with respect to the total weight of plum butter.

Preferably, the pistachio butter according to the invention comprises between 30% and 50%, more preferably between 34% and 46%, by weight of hydrogenated pistachio oil and between 50% and 70%, more preferably between 54% and 66%, by weight of pistachio oil, with respect to the total weight of pistachio butter. Preferably, the pistachio butter according to the invention comprises approximately 0.3% by weight of vitamin E, with respect to the total weight of pistachio butter.

Preferably, the almond butter according to the invention comprises between 30% and 50%, more preferably between 34% and 46%, by weight of hydrogenated almond oil and between 50% and 70%, more preferably between 54% and 66%, by weight of almond oil, with respect to the total weight of almond butter. Preferably, the almond butter according to the invention comprises approximately 0.2% by weight of vitamin E, with respect to the total weight of almond butter.

Preferably, the apricot butter according to the invention comprises between 25% and 45%, more preferably between 29% and 41%, by weight of hydrogenated apricot oil and between 55% and 75%, more preferably between 59% and 71%, by weight of apricot oil, with respect to the total weight of apricot butter. Preferably, the apricot butter according to the invention comprises approximately 0.2% by weight of vitamin E, with respect to the total weight of apricot butter.

Preferably, the argan butter according to the invention comprises between 35% and 55%, more preferably between 39% and 51%, by weight of hydrogenated argan oil and between 45% and 65%, more preferably between 49% and 61%, by weight of argan oil, with respect to the total weight of argan butter. Preferably, the argan butter according to the invention comprises approximately 0.3% by weight of vitamin E, with respect to the total weight of argan butter.

Preferably, the avocado butter according to the invention comprises between 20% and 40%, more preferably between 27% and 38%, by weight of hydrogenated avocado oil and between 60% and 80%, more preferably between 62% and 73%, by weight of avocado oil, with respect to the total weight of avocado butter. Preferably, the avocado butter according to the invention comprises approximately 0.2% by weight of vitamin E, with respect to the total weight of avocado butter.

Preferably, the oat butter according to the invention comprises between 35% and 55%, more preferably between 40% and 50%, by weight of hydrogenated oat oil and between 45% and 65%, more preferably between 50% and 60%, by weight of oat oil, with respect to the total weight of oat butter. Preferably, the oat butter comprises approximately 0.2% by weight of vitamin E, with respect to the total weight of oat butter.

Preferably, the coconut butter according to the invention comprises between 80% and 98%, more preferably between 85% and 95%, by weight of hydrogenated coconut oil and between 2% and 20%, more preferably between 5% and 15%, by weight of coconut oil, with respect to the total weight of coconut butter. Preferably, the coconut butter according to the invention comprises approximately 0.2% by weight of vitamin E, with respect to the total weight of coconut butter.

Preferably, the olive butter according to the invention comprises between 30% and 50%, more preferably between 37% and 48%, by weight of hydrogenated olive oil and between 50% and 70%, more preferably between 52% and 63%, by weight of olive oil, with respect to the total weight of olive butter. Preferably, the olive butter according to the invention comprises approximately 0.2% by weight of vitamin E, with respect to the total weight of olive butter.

Preferably, the butter according to the invention has a melting point of between 25 and 70° C. The melting point of the butter according to the invention can be measured by any method well known to a person skilled in the art. By way of example, the melting point of the butter according to the invention can be measured by differential scanning calorimetry.

By way of example, the almond butter, apricot butter, argan butter, avocado butter, plum butter, pistachio butter, oat butter and olive butter according to the invention have a melting point of between 50 and 70° C., preferably between 55 and 70° C.

By way of example, the coconut butter according to the invention has a melting point of between 26 and 35° C., preferably between 30 and 35° C.

Preferably, the butter according to the invention exhibits a viscosity of at least 3000 mPa·s, measured at the crystallization point of the butter.

Preferably also, the butter according to the invention exhibits a viscosity of between 3000 and 81 500 mPa·s, more preferably between 3000 and 25 000 mPa·s, even more preferably between 3000 and 10 000 mPa·s, measured at the crystallization point of the butter.

The viscosity can be measured according to any method well known to a person skilled in the art. Preferably, the viscosity of the butters according to the invention is measured using a rheometer. It is possible to mention, as example of rheometer, the Physica MCR 301 rheometer of the Anton Paar brand. Preferably, the viscosity measurement is carried out at a temperature of 80° C. to 20° C. with a shear rate of 38.2 s'.

Table 1 below is given as example of viscosities of butters according to the invention:

TABLE 1

| Butter according to the invention | Crystallization point (° C.) | Viscosity (mPa · s) measured at the crystallization point |
| --- | --- | --- |
| Plum butter | 32.3 | 24 000 |
| Hazelnut butter | 35.5 | 81 100 |
| Oat butter | 41.8 | 9140 |
| Pistachio butter | 41.8 | 6120 |
| Almond butter | 38.6 | 6160 |
| Apricot butter | 26 | 20 500 |
| Argan butter | 32.3 | 12 300 |
| Avocado butter | 41.8 | 8030 |
| Hemp butter | 38.6 | 3280 |
| Olive butter | 35.5 | 6630 |

Preferably, the butter according to the invention has a peroxide value, expressed as mEq $O_2$/kg, of less than or equal to 10, preferably of between 0.1 and 5. The peroxide value corresponds to the degree of oxidation of the unsaturated fatty acids of the sample. The peroxide value can be measured according to any method well known to a person skilled in the art. By way of example of method for measuring the peroxide value, it is possible to use the standardized method NF EN ISO 3960. This method is based on the titrating of the iodine released by potassium iodide in an acidic medium.

Preferably, the butter according to the invention has an iodine number, expressed as g $I_2$/100 g, of between 0 and 82. The iodine number corresponds to the weight of molecular iodine capable of attaching to the unsaturations of the fatty acids contained in one hundred grams of fatty substance. The iodine number can be measured according to any method well known to a person skilled in the art. By way of example of method for measuring the iodine number, it is possible to use the standardized method NF ISO 3961. This method is based on the titrating of the iodine released by potassium iodide.

By way of example, the almond butter, apricot butter, argan butter, avocado butter, plum butter, pistachio butter, oat butter and olive butter according to the invention have an iodine number of between 40 and 80, preferably between 45 and 75.

By way of example, the coconut butter according to the invention has an iodine number of between 0 and 3, preferably of less than 1.

Preferably, the butter according to the invention has an acid number, expressed as mg KOH/kg, of less than or equal to 7, preferably of between 0.1 and 5. The acid number can be measured by any method well known to a person skilled in the art. By way of example of method for measuring the acid number, it is possible to mention the standardized method NF EN ISO 660. The principle of this method is based on the quantitative determination of the acidity of the sample dissolved in an alcoholic solution by an ethanolic potassium hydroxide solution.

Preferably, the butter according to the invention has an ash content, expressed as % of ash, of less than or equal to 0.1, preferably of between 0.005 and 0.01. By way of example of method of determination of the ash content, it is possible to mention the standardized method NF ISO 6884. The principle of this method is based on the incineration of the sample at a temperature of between 550° C. and 660° C. until it is devoid of carbonaceous particles. The inorganic residue obtained, corresponding to the ash, is subsequently weighed.

Preferably, the butter according to the invention is intended to be used as cosmetic, that is to say directly on the skin or the hair, or in a cosmetic composition, in particular for cleaning, moisturizing and protecting the skin and the hair or also for giving body to the cosmetic composition.

Advantageously, the butter according to the invention exhibits at least one of the following properties: nourishing, moisturizing, healing, tranquilizing, soothing, softening, of regeneration of the skin, of improving the elasticity of the skin.

Process for the Preparation of Butter

Preferably, the process for the preparation of butter according to the invention comprises at least one step of hydrogenation of a vegetable oil according to the invention.

The hydrogenation of vegetable oil is well known to a person skilled in the art. As intended herein, the term "hydrogenation" relates to the process by which hydrogen is added to the double bonds of unsaturated organic compounds, in particular the fatty acids of which vegetable oils are composed. Typically, the oil is reacted with hydrogen at high temperature and high pressure in the presence of a catalyst. The oil is kept stirred in a closed reactor in the presence of a catalyst, into which hydrogen is injected batchwise under a pressure of between 1 and 5 bars at a temperature of between 100 and 250° C., more preferably between 110 and 180° C. Advantageously and unexpectedly, the hydrogenation of a vegetable oil according to the invention at a temperature as defined above makes it possible to obtain a butter having the properties required for use in cosmetic compositions.

Preferably, the source of molecular hydrogen for the hydrogenation reaction according to the invention is gaseous molecular hydrogen.

Preferably, the hydrogenation reaction according to the invention is carried out at a temperature of between 100° C. and 250° C., preferably between 180° C. and 210° C., and at a pressure of between 1 and 5 bars.

Preferably, the hydrogenation reaction according to the invention is carried out in the presence of a catalyst. Preferably, the catalyst is a heterogeneous catalyst. By way of example of catalyst suitable for the hydrogenation reaction according to the invention, it is possible to mention the metals from the platinum group, in particular platinum, palladium, rhodium and ruthenium, nickel-based catalysts, such as Raney nickel or Urushibara nickel, and catalysts based on cobalt, on iron and on copper or zinc chromite. Preferably, the catalyst used is a catalyst of Raney nickel type.

Preferably, the amount of catalyst used in the hydrogenation reaction according to the invention is comprised between 0.01% and 2%, preferably between 0.01% and 0.5%, by weight, with respect to the weight of the vegetable oil which it is desired to hydrogenate.

Preferably, the reaction of hydrogenation of the vegetable oil according to the invention has the effect of rendering the vegetable oil solid or semisolid.

Preferably, the process according to the invention comprises a step of addition of vegetable oil to the hydrogenated vegetable oil. Preferably, the vegetable oil added is identical to the vegetable oil which has been hydrogenated. Preferably, the vegetable oil is added slowly to the hydrogenated oil still warm in the reactor.

Preferably, the addition of vegetable oil is carried out under a stream of nitrogen and with stirring. The mixture is homogenized with stirring for a period of time of at least 30 minutes and the temperature is lowered. Preferably, this stage makes it possible to obtain the consistency of a butter.

The amount of hydrogenated vegetable oil according to the invention is preferably between 20% and 98%, more preferably between 30% and 90%, by weight, with respect to the total weight of butter.

Preferably, the amount of vegetable oil added is between 2% and 80% by weight, preferably between 10% and 70%, with respect to the total weight of butter.

Preferably, the butter prepared or capable of being prepared by the process according to the invention comprises between 20% and 98%, more preferably between 30% and 90%, by weight of hydrogenated vegetable oil, with respect to the total weight of the butter.

Preferably, the butter prepared or capable of being prepared by the process comprises between 2% and 80%, more preferably between 10% and 70%, by weight of vegetable oil, with respect to the total weight of butter.

By way of example, the plum oil, pistachio oil, almond oil, apricot oil, argan oil, avocado oil, oat oil or olive oil is added to the corresponding hydrogenated oil in an amount of between 45% and 80%, preferably between 50% and 72%, by weight, with respect to the total weight of butter.

By way of example, the coconut oil is added to the hydrogenated coconut oil in an amount of between 2% and 20%, preferably between 5% and 15%, by weight, with respect to the total weight of butter.

Preferably, the process according to the invention comprises at least one step of deodorization.

According to one embodiment of the invention, the step of deodorization is carried out on the hydrogenated vegetable oil according to the invention. The butter obtained according to the invention thus has the odor of the vegetable oil added to the deodorized hydrogenated vegetable oil.

According to another embodiment of the invention, the deodorization step is carried out on the butter according to the invention, that is to say after the step of addition of vegetable oil to the hydrogenated vegetable oil.

The deodorization consists of the removal of the odorous substances. The deodorization can be carried out according to any method well known to a person skilled in the art. Typically, the deodorization is based on the injection of a stream of steam or of nitrogen into the oil heated to a temperature of between 150 and 250° C. under vacuum of between 1 and 20 mbar, preferably between 2 and 6 mbar. The volatile substances responsible for the odors of the oil are separated by virtue of the stream and then removed using a vacuum pump and a cooling operation.

Preferably, the deodorization according to the invention is carried out at a temperature of between 160 and 230° C., preferably under vacuum of between 2 and 20 mbar, preferably of approximately 5 mbar. The deodorization according to the invention can be carried out under a stream of steam or under a stream of nitrogen, for a period of time preferably of less than three hours, more preferably of less than two and a half hours.

Preferably, the process for the preparation of butter selected from hazelnut butter, cherry plum butter and plum butter comprises a step of deodorization of the hydrogenated vegetable oil. Advantageously, the butter obtained has the odor of the vegetable oil added to the deodorized hydrogenated vegetable oil.

Preferably, the process according to the invention additionally comprises a step of addition of vitamin E. Preferably, the amount of vitamin E added to the butter is between 0.1% and 0.5% by weight, with respect to the total weight of butter. More preferably, the amount of vitamin E added to the butter is between 0.2% and 0.3% by weight, with respect to the total weight of butter.

Preferably, the butter according to the invention intended to be used in cosmetic compositions is prepared by the process according to the invention as defined above.

Cosmetic Compositions

Preferably, at least one butter according to the invention is used in cosmetic compositions as cosmetic ingredient, in particular as texturizing agent, nourishing agent, emollient agent or conditioner, or for contributing a melting effect.

Preferably, the cosmetic composition according to the invention comprises at least one butter according to the invention selected from the group consisting of almond butter, apricot butter, argan butter, avocado butter, coconut butter, olive butter, macadamia butter, jojoba butter, hazelnut butter, sea buckthorn butter, fig butter, raspberry butter, sesame butter, oat butter, cherry plum butter, desert date butter, plum butter, pistachio butter, hemp butter and the mixture thereof.

Preferably, the cosmetic composition according to the invention comprises at least one butter according to the invention selected from the group consisting of almond butter, apricot butter, argan butter, avocado butter, coconut butter, plum butter, pistachio butter, oat butter, olive butter and of the mixture thereof.

The cosmetic compositions according to the invention can be of any form well known to a person skilled in the art. By way of example, the cosmetic compositions according to the invention can be in the cream, milk, butter, emulsion, balm, stick, gel, solid or oil form or any other form well known to a person skilled in the art.

Preferably, the cosmetic compositions comprising at least one butter according to the invention are selected from the group consisting of hygiene products, such as shower gels, personal cleansing gels, face cleansers, makeup removers, soaps, shampoos, solid shampoos or deodorants; face care products, such as antiwrinkle creams, day creams, night creams, moisturizing creams, masks for the face or the outline of the eyes, balms for the lips or oils for the face; hair products, such as conditioners, masks for the hair or the scalp, oils for the hair, gels, treating creams for dry hair having damaged ends or beard maintenance products; makeup products, such as foundation, lipstick, CC creams, BB creams, concealers, self-tanning products, complexion illuminators or mattifying agents; sun products, such as sun or aftersun creams, oils or lotions; care products for the body, such as oils, balms, creams or milks for the body, creams for the hands or anti-stretchmark creams; and massage products, such as massage oils and balms.

The cosmetic compositions according to the invention can additionally comprise at least one additional compound selected from the group consisting of an emulsifier, a texture agent, an emollient, a solvent, a humectant, a gelling agent, a preservative, a pH regulator, a texturizing agent, a dye, a fragrance, a buffer, an antioxidant, a pigment, a curing agent, a filler, a surfactant, a lubricant, a hair conditioner, an anti-irritant agent, an anti-inflammatory active principle, an anti-tautness agent, a mattifying agent and a co-emulsifier. The present invention is illustrated by the following non-limiting examples.

EXAMPLES

Example 1: Preparation of Avocado Butter 1.1. Hydrogenation

The avocado oil is introduced into a 300 l pressurized reactor at a temperature of 100° C. A heterogeneous hydrogenation catalyst of the type of Raney nickel on carbon (Pricat 9910® Johnson Matthey, 22% of Ni) is also introduced into the reactor.

The temperature of the reactor is high and maintained at 210° C. in order to retain a core reaction temperature of 180° C. 2 bars of hydrogen are introduced into the reactor. The mixture is stirred for 15 minutes. Stirring is halted and the hydrogen is solely degassed until a pressure of zero is reached. 5 bars of hydrogen are reintroduced into the reactor. Stirring is started and the hydrogen consumption is monitored. When there is no longer consumption on the manometer of the hydrogen cylinder, the temperature of the reactor is lowered to 110° C. The hydrogen is slowly degassed.

1.2. Formulation

In the 300 l reactor, the avocado oil is slowly added to the still warm (110° C.) hydrogenated avocado oil under a stream of nitrogen in order to limit the oxidation of the oil. Stirring is started and the mixture is homogenized for 30 minutes. The temperature is lowered to 90° C. Vitamin E (Bioxan T90) is added. A 30 l cartridge filter press is connected to the outlet of the reactor and the oil is filtered.

The proportions of hydrogenated avocado oil and of avocado oil in the avocado butter are presented in table 2 below.

TABLE 2

| % by weight of hydrogenated oil, with respect to the total weight of butter | % by weight of oil, with respect to the total weight of butter | % by weight of vitamin E, with respect to the total weight of butter |
| --- | --- | --- |
| 30-35 | 65-70 | 0.2-0.3 |

1.3. Deodorization

The mixture is deodorized by raising the temperature to 160° C. under a vacuum of 5 mbar under a stream of steam for 1 h 30. The deodorized butter thus obtained is cooled to 70° C.

1.4. Characterization

The melting point of the butter is measured. The peroxide value, expressed as mEq $O_2$/kg, is measured according to the standardized method NF EN ISO 3960. The iodine number, expressed as g $I_2$/100 g, is measured according to the standardized method NF ISO 3961. The acid number, expressed as mg KOH/g, is measured according to the standardized method NF EN ISO 660. The ash content, expressed as % of ash, is measured according to the standardized method NF ISO 6884.

The results are presented in the following table 3:

TABLE 3

| Melting point | Peroxide value (mEq $O_2$/kg) | Acid number (mg KOH/g) | Iodine number (g $I_2$/100 g) | Ash (% of ash) |
| --- | --- | --- | --- | --- |
| 58-64 | <10 | ≤5 | 47-63 | ≤0.1 |

The fatty acid profile of the avocado butter is presented in table 4 below:

TABLE 4

| Fatty acid | % of fatty acid in the butter |
| --- | --- |
| Linoleic acid | 4.0-12.0 |
| Linolenic acid | 0.0-2.0 |
| Oleic acid | 30.0-50.0 |
| Palmitic acid | 12.0-28.0 |
| Palmitoleic acid | 0.0-10.1 |
| Stearic acid | 15.0-35.0 |

Example 2: Treating Cream for Dry Hair Having Damaged Ends

The composition of a cream for dry hair having damaged ends comprising the avocado butter according to the invention is presented in Table 5 below.

TABLE 5

| Name | % by weight, with respect to the total weight of product |
| --- | --- |
| Cetearyl alcohol 60%, dipalmitoylethyl hydroxyethylamonium methosulfate 25%, ceteareth-20 15% | 6 |
| Cetearyl alcohol | 2 |
| Avocado butter according to the invention | 2 |
| Deodorized walnut oil | 5 |
| Purified water | 78.25 |
| Glycerine | 5 |
| Hydroxyethylcellulose | 0.5 |
| Sodium benzoate | 0.5 |
| Fragrance | 0.75 |

TABLE 5-continued

| Name | % by weight, with respect to the total weight of product |
|---|---|
| Citric acid | q.s. for |

The avocado butter obtained according to the invention gives a rich texture to the cream and confers nourishing properties on it.

Example 3: Hair Mask

A hair mask formulation comprising almond butter and argan butter according to the invention is presented in table 6 below:

TABLE 6

| Name | % by weight, with respect to the total weight of product |
|---|---|
| Cetostearyl alcohol, dipalmitoylethyl hydroxyethylmonium methosulfate, ceteareth-20 | 8 |
| Almond butter according to the invention | 3 |
| Argan butter according to the invention | 2 |
| Purified water | 80.49 |
| Glycerine | 5 |
| Sodium benzoate | 0.50 |
| Dye | 0.0013 |
| Dye | 0.0024 |
| Fragrance | 1.00 |
| Citric acid | q.s. for |

The almond butter according to the invention protects the hair and gives it softness. The argan butter according to the invention nourishes and moisturizes the hair and contributes suppleness to it.

The invention claimed is:

1. A single vegetable oil butter, consisting of:
   (a) between 2% and 80% by total weight of the butter of the single vegetable oil which is not hydrogenated; and
   (b) between 20% and 98% by total weight of the butter of the same single vegetable oil, which is hydrogenated; and
   (c) optionally vitamin E.

2. The butter according to claim 1, which comprises essentially no water or hydrophilic phase.

3. The butter according to claim 1, further comprising between 0.2% and 0.3% by total weight of the butter of vitamin E.

4. The butter according to claim 1, wherein the single vegetable oil is selected from the group consisting of plum oil, pistachio oil, almond oil, apricot oil, argan oil, avocado oil, olive oil, coconut oil and oat oil.

5. The butter according to claim 4, wherein the single vegetable oil is selected from the group consisting of plum oil, pistachio oil, almond oil, apricot oil, argan oil, avocado oil, oat oil and olive oil which comprises between 20% and 55% by weight of hydrogenated vegetable oil and between 45% and 80% by weight of non-hydrogenated vegetable oil, with respect to the total weight of butter.

6. The butter according to claim 4, wherein the single vegetable oil is coconut which comprises between 2% and 20% by weight of non-hydrogenated coconut vegetable oil and between 80% and 98% by weight of hydrogenated coconut vegetable oil, with respect to the total weight of butter.

7. A butter according to claim 1, which is made using the steps:
   (a) hydrogenating or partially hydrogenating a portion of the single vegetable oil;
   (b) mixing non-hydrogenated vegetable oil with the hydrogenated vegetable oil to obtain a butter; and
   (c) optionally, deodorizing the butter.

8. A cosmetic composition comprising at least one butter as defined in claim 1.

9. A cream, milk, emulsion, balm, stick, gel, solid, or oil cosmetic composition comprising the butter according to claim 8.

10. The cosmetic composition according to claim 8, which is selected from the group consisting of hygiene products, face care products, hair products, makeup products, sun products, care products for the body and massage products.

11. The cosmetic composition according to claim 8, further comprising at least one additional compound selected from the group consisting of an emulsifier, a texture agent, an emollient, a solvent, a humectant, a gelling agent, a preservative, a pH regulator, a texturizing agent, a dye, a fragrance, a buffer, an antioxidant, a pigment, a curing agent, a filler, a surfactant, a lubricant, a hair conditioner, an anti-irritant agent, a mattifying agent and a co-emulsifier.

* * * * *